(12) United States Patent
Auvin et al.

(10) Patent No.: US 9,676,752 B2
(45) Date of Patent: Jun. 13, 2017

(54) IMIDAZOLIDINE-2,4-DIONE DERIVATIVES

(71) Applicant: IPSEN PHARMA S.A.S., Boulogne-Billancourt (FR)

(72) Inventors: Serge Auvin, Palaiseau (FR); Christophe Lanco, Dourdan (FR); Qi Chao, San Diego, CA (US); Kaichun Gu, Shanghai (CN)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 0 days.

(21) Appl. No.: 15/108,757

(22) PCT Filed: Dec. 31, 2013

(86) PCT No.: PCT/CN2013/091092
§ 371 (c)(1),
(2) Date: Jun. 28, 2016

(87) PCT Pub. No.: WO2015/100613
PCT Pub. Date: Jul. 9, 2015

(65) Prior Publication Data
US 2016/0318902 A1    Nov. 3, 2016

(51) Int. Cl.
*C07D 401/14*    (2006.01)
*C07D 233/74*    (2006.01)

(52) U.S. Cl.
CPC .......... *C07D 401/14* (2013.01); *C07D 233/74* (2013.01)

(58) Field of Classification Search
CPC ............................ C07D 401/14; C07D 233/74
See application file for complete search history.

(56) References Cited

U.S. PATENT DOCUMENTS 7,759,366 B2    7/2010    Jaehne et al.
8,624,037 B2 *    1/2014    Bigg .................... C07D 403/06
                                              548/311.1

FOREIGN PATENT DOCUMENTS

CN        102428079        4/2014
WO        2008/017381      2/2008

OTHER PUBLICATIONS

Schafer et al. Drug Discovery Today, 2008, 13 (21/22), 913-916.*
Horig et al. Journal of Translational Medicine 2004, 2(44), p. 1-8.*
International Search Report, issued Sep. 11, 2014, in PCT/CN2013/091092.

* cited by examiner

*Primary Examiner* — Yong Chu
(74) *Attorney, Agent, or Firm* — Hunton & Williams LLP

(57) ABSTRACT

Imidazolidine-2,4-dione derivatives of formula (I):

The compounds have anti-proliferative activity and are useful for treating pathological states and diseases linked to an abnormal cell proliferation such as cancer.

14 Claims, No Drawings

IMIDAZOLIDINE-2,4-DIONE DERIVATIVES

CROSS-REFERENCE TO RELATED APPLICATIONS

This application is the U.S. National Phase of International Patent Application No. PCT/CN2013/091092, filed Dec. 31, 2013, the contents of which are hereby incorporated by reference in their entirety.

FIELD OF THE INVENTION

A subject of the present application is novel imidazolidine-2,4-dione derivatives. These products have an anti-proliferative activity. They are particularly useful for treating the pathological states and the diseases linked to an abnormal cell proliferation such as cancers.

The invention also relates to the pharmaceutical compositions containing said products and their use for the preparation of a medicament.

STATE OF THE ART

Nowadays, cancer still constitutes one of the major causes of death despite there being numerous molecules on the market.

It is therefore necessary to identify more powerful novel molecules allowing a better anti-tumour response, specifically by a good inhibitory activity on the proliferation of tumour cell colonies.

Such molecules are therefore particularly useful for treating the pathological states linked to an abnormal cell proliferation. They can therefore be used for the treatment of tumours or cancers, for example, those of the oesophagus, the stomach, the intestines, the rectum, the oral cavity, the pharynx, the larynx, the lung, the colon, the breast, the cervix uteri, the corpus endometrium, the ovaries, the prostate, the testes, the bladder, the kidneys, the liver, the pancreas, the bones, the connective tissues, the skin such as melanomas, the eyes, the brain and the central nervous system, as well as cancer of the thyroid gland, leukaemia, Hodgkin's disease, non-Hodgkin's lymphomas, multiple myelomas and other cancers.

It is of particular interest to find therapies for hormone-dependent cancers, for tumours expressing androgen receptors, for cancers of the breast and prostate.

The use of the anti-androgens in prostate cancer is based on their property of entering into competition with the natural agonists of the androgen receptor. However, the efficacy of these anti-androgens appears to be limited over time, the patients rapidly escaping the treatment.

Several hypotheses regarding this failure have been developed showing an agonist activity in place of an antagonist activity of these molecules (Veldscholte J, Berrevoets C A, Brinkmann A O, Grootegoed J A, Mulder E. Biochemistry 1992 Mar. 3; 31(8):2393-9). For example, nilutamide is capable of stimulating the growth of human prostate cancer cells in culture. In addition to these experimental indications, clinical data also support this deleterious role of the anti-androgens (Akimoto S.; Antiandrogen withdrawal syndrome Nippon Rinsho. 1998 August; 56(8):2135-9. Paul R, Breul J. Antiandrogen withdrawal syndrome associated with prostate cancer therapies: incidence and clinical significance Drug Saf 2000 November; 23(5):381-90). Resistance to anti-androgen therapies can also occur through overexpression of the androgen receptor, which then becomes highly sensitive to low levels of androgens. Another way by which prostate cancer cells become resistant is via the emergence of mutations in the androgen receptor that becomes responsive to other kinds of steroids than androgens, or deletions of part of the androgen receptor, which then becomes constitutively activated.

In WO2010/119194 the Applicant had identified compounds showing an anti-proliferative activity for the prostatic tumour which does not show agonist activity at concentrations where the nilutamide behaves as an agonist. This difference in these compounds' behaviour with respect to proliferation compared with that of nilutamide is supported by their ability to induce the disappearance of androgen receptors in their protein form. Nilutamide has no effect on this receptor level. The properties of these molecules allow better management of prostate cancer avoiding the failure of current anti-androgens.

However, these molecules have a poor aqueous solubility, which makes them hard to formulate as an effective medicine. In fact, in pharmacokinetic studies in animals, the plasma exposure did not increase with dose due to the limited solubility in formulations.

Therefore there is a need to identify compounds showing a good anti-proliferative activity for the prostatic tumour, no escape from treatment and which can also be easily formulated, by having a better aqueous solubility.

The Applicant has identified new compounds showing an anti-proliferative activity for the prostatic tumour with no escape from treatment which surprisingly does show a good aqueous solubility.

The properties of these novel molecules must allow to easily formulate the compounds in pharmaceutically acceptable formulations while keeping the same biological profile.

Moreover, the compounds of the present invention can also be used for treating pathologies linked to the presence of androgen receptors such as for example benign prostatic hyperplasia, prostamegaly, acne, androgenic alopecia, hirsutism etc.

SUMMARY OF THE INVENTION

A subject of the invention is therefore the compounds of general formula (I)

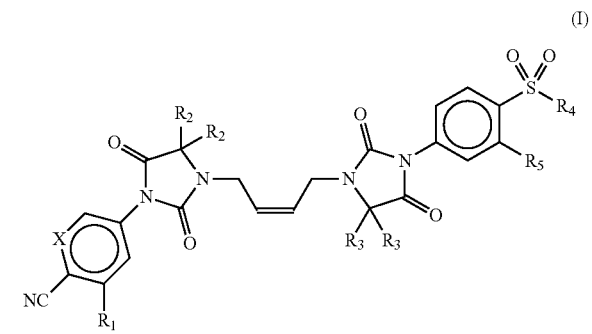

wherein:
$R^1$ is a —$CF_3$ group or a halogen atom;
$R^2$ is a ($C_1$-$C_6$)alkyl group or the two $R^2$ together form a ($C_3$-$C_6$)cycloalkyl group;
X is CH or N;
$R^3$ is an hydrogen atom or a ($C_1$-$C_6$)alkyl group or the two $R^3$ together form a ($C_3$-$C_6$)cycloalkyl group;
$R^4$ is a ($C_1$-$C_6$)alkyl group;
$R^5$ is a —$CF_3$ group or a halogen atom;
or a salt thereof.

Preferably, R² represents a (C₁-C₆)alkyl group. More preferably, R² is a methyl group.

Alternatively, the two R² together form a (C₃-C₆)cycloalkyl group.

Preferably, R³ is a (C₁-C₆)alkyl group. More preferably, R³ is a methyl group.

Alternatively, the two R³ together form a (C₃-C₆)cycloalkyl group.

Preferably, R⁴ is a (C₁-C₃)alkyl group. More preferably, R⁴ is a methyl group. Alternatively, R⁴ is an ethyl group.

Preferably, R⁵ is a —CF₃ group.

Preferably, R¹ is a —CF₃ group.

Preferably, the compound of formula I is chosen from
(Z)-4-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2,5-dioxoimidazolidin-1-yl)-2-(trifluoromethyl)benzonitrile;
(Z)-5-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2,5-dioxoimidazolidin-1-yl)-3-(trifluoromethyl)picolinonitrile; or
(Z)-4-(4,4-dimethyl-3-(4-(3-(4-(methylsulfonyl)-3-(trifluoromethyl)phenyl)-2,4-dioxoimidazolidin-1-yl)but-2-en-1-yl)-2,5-dioxoimidazolidin-1-yl)-2-(trifluoromethyl)benzonitrile,
or a pharmaceutically acceptable salt thereof.

For example, the compound of formula I is (Z)-4-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2,5-dioxoimidazolidin-1-yl)-2-(trifluoromethyl)benzonitrile or a pharmaceutically acceptable salt thereof.

Another subject of the invention is a compound of formula I as defined above, as a medicament.

Another subject of the invention is a pharmaceutical composition containing, as active ingredient, at least one compound of formula (I) as defined above, in combination with a pharmaceutically acceptable support.

Another subject of the invention is the use of a compound of formula (I) as defined above, for the preparation of a medicament intended to treat cancers.

Preferably the medicament is intended to treat a hormone-dependent cancer.

More preferably, the medicament is intended to treat a cancer expressing androgen receptors.

More preferably, the medicament is intended to treat a breast or prostate cancer, preferably a prostate cancer.

DETAILED DESCRIPTION OF EMBODIMENTS OF THE INVENTION

Therefore a subject of the invention is the compounds of general formula (I)

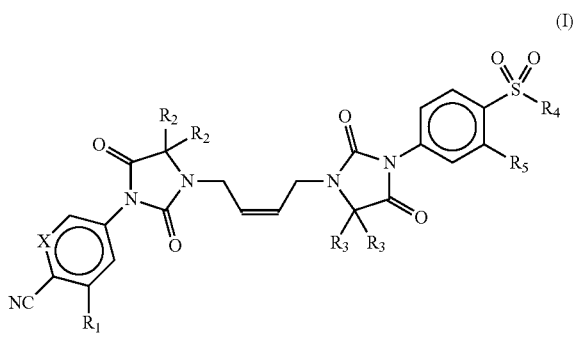

(I)

wherein:

R¹ is a —CF₃ group or a halogen atom;

R² is a (C₁-C₆)alkyl group or the two R² together form a (C₃-C₆)cycloalkyl group;

X is CH or N;

R³ is an hydrogen atom or (C₁-C₆)alkyl group or the two R³ together form a (C₃-C₆)cycloalkyl group;

R⁴ is a (C₁-C₆)alkyl group;

R⁵ is a —CF₃ group or a halogen atom;

or a pharmaceutically acceptable salt thereof.

By pharmaceutically acceptable salt, is meant in particular addition salts of inorganic acids such as hydrochloride, hydrobromide, sulphate, phosphate, diphosphate and nitrate or organic acids such as acetate, maleate, fumarate, tartrate, succinate, citrate, lactate, methanesulphonate, benzenesulphonate, p-toluenesulphonate, pamoate and stearate. Also included within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

In the definitions indicated above, the expression halogen represents the fluoro, chloro, bromo or iodo radical, preferably chloro, fluoro or bromo. More preferably halogen represents the chloro radical.

Unless otherwise specified, the term alkyl within the meaning of the present invention represents a linear or branched alkyl radical comprising between 1 and 6 carbon atoms such as the methyl, ethyl, propyl, isopropyl, butyl, isobutyl, sec-butyl and tert-butyl, pentyl or amyl, isopentyl, neopentyl, hexyl or isohexyl radicals. The alkyl radical is a (C₁-C₆)alkyl radical, i.e. representing an alkyl radical having 1 to 6 carbon atoms as defined above, or preferably a (C₁-C₄)alkyl radical representing an alkyl radical having 1 to 4 carbon atoms such as for example the methyl, ethyl, propyl, isopropyl, butyl, isobutyl, sec-butyl and tert-butyl radicals. Very preferentially, the alkyl radical is the methyl radical.

By cycloalkyl unless otherwise specified, is meant a saturated cyclic carbon radical comprising 3 to 6 members such as the cyclopropyl or cyclobutyl.

DETAILED DESCRIPTION OF THE PREPARATION PROCESSES

A) Preparation of Compounds of the General Formula I:

Compounds of formula I can be prepared as shown in the scheme A, below. Compounds of formula I in which R¹, R², R³, R⁴, R⁵ and X are as defined above can be prepared by N-alkylation of a compound of general formula III.₂ in which R³, R⁴ and R⁵ are as defined above by a compound of general formula II.₁ in which R¹, R² and X are as defined above. The reaction can be conducted at a temperature between 0 and 80° C., preferably between 15 and 35° C. For instance the reaction can be conducted at room temperature. The reaction can be conducted in an aprotic solvent such as for instance acetonitrile, dimethylformamide or tetrahydrofurane. The reaction can be conducted in presence of a mineral or organic base. A convenient mineral base can be for instance K₂CO₃, Na₂CO₃, NaH, or KH. A convenient organic base can be for instance a tertiary amine such as for instance triethylamine or N,N-diisopropylethylamine.

Scheme A

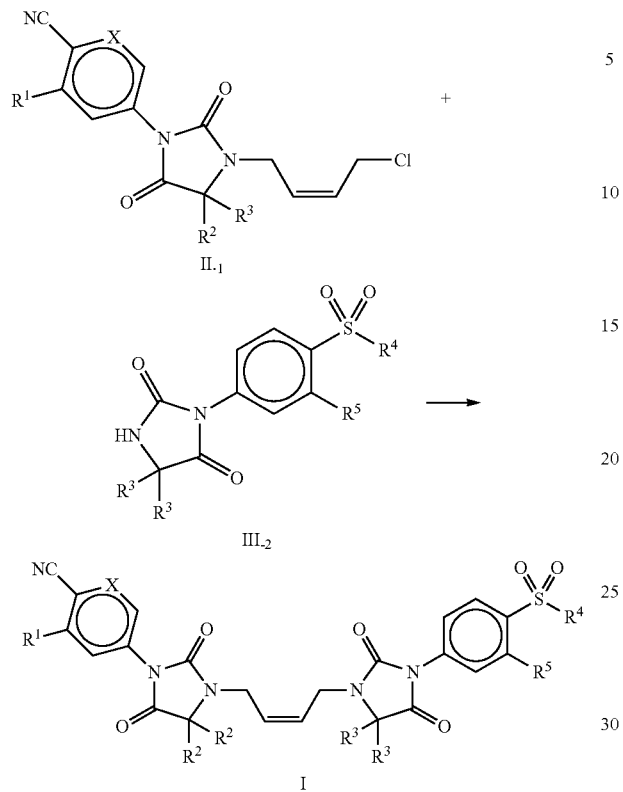

B) Preparation of the Intermediate Compounds of General Formula II.$_1$:

Compounds of general formula II.$_1$ can be prepared as shown in scheme B, below. Compounds of general formula II.$_1$ in which $R^1$, $R^2$ and X are as defined above can be prepared by N-alkylation of a compound of general formula III.$_1$ in which $R^1$, $R^2$ and X are as defined above by an excess of (Z)-1,4-dichlorobut-2-ene. The reaction can be conducted at a temperature between 0 and 80° C., preferably between 15 and 35° C. For instance the reaction can be conducted at room temperature. The reaction can be conducted in an aprotic solvent like for instance acetonitrile, dimethylformamide or tetrahydrofurane. The reaction can be conducted in presence of a mineral or organic base. A convenient mineral base can be for instance $K_2CO_3$, $Na_2CO_3$, NaH, or KH. A convenient organic base can be for instance a tertiary amine like for instance triethylamine or N,N-diisopropylethylamine.

Scheme B

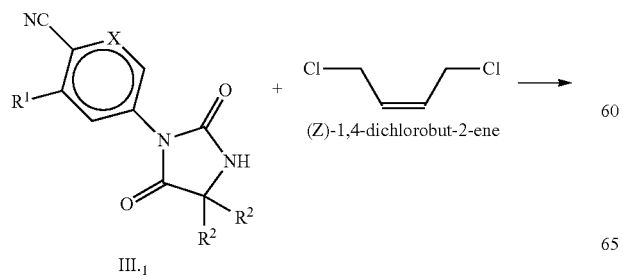

(Z)-1,4-dichlorobut-2-ene

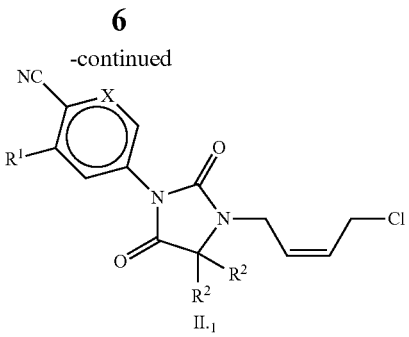

C) Preparation of the Intermediates Compounds of General Formula III.$_1$:

C.1) Preparation of Compounds of General Formula III.$_1$ Wherein X is CH

Compounds of formula III.$_1$ can be prepared as described in the scheme C.1 below according to i) or ii).

i) Compounds of the general formula III.$_1$ in which $R^1$ and $R^2$ are as defined above and X is CH can be prepared by reaction of an hydantoin of general formula V.$_1$ in which $R^2$ is as defined above and a compound of the general formula IV.$_1$ in which $R^1$ is as defined above, X is CH and Gf$_1$ is an atom of iodine or bromine. The reaction can be conducted at a temperature between 80 and 150° C. in a polar aprotic solvent, for instance dimethylformamide. The reaction can be conducted in presence of copper derivative, for instance copper oxide; or ii) Compounds of the general formula III.$_1$ in which $R^1$ and $R^2$ are as defined above and X is CH can be prepared by reaction of an hydantoin of general formula V.$_1$ in which $R^2$ is as defined above and a compound of general formula IV.$_1$ in which $R^1$ is as defined above, X is CH and Gf$_1$ is an atom of fluorine. The reaction can be conducted in a aprotic solvent like for instance acetonitrile, dimethylformamide or tetrahydrofurane. The reaction is conducted in presence of a mineral or organic base. A convenient mineral base is for instance $K_2CO_3$, $Na_2CO_3$, NaH, or KH. A convenient organic base can be for instance a tertiary amine like for instance triethylamine or N,N-diisopropylethylamine.

Scheme C.1

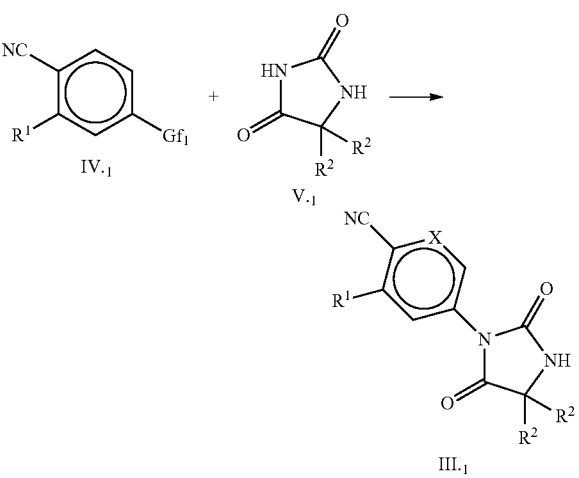

C.2) Preparation of Compounds of General Formula III.$_1$ Wherein X is N

Compounds described in the general formula III.$_1$ can be prepared as shown in the scheme C.2, below. Compounds of general formula III.$_1$ in which R$^1$, R$^2$ are as define above and X is N can be prepared by treatment of a compound of general formula III.$_{1.1}$ in which R$^1$, R$^2$ are as define above and X is N with a cyanide salt such as for instance Zn(CN)$_2$. The reaction can be conducted at a temperature between 80 and 150° C. in a polar aprotic solvent like for instance dimethylformamide. The reaction can be conducted in presence of a palladium complex derivative like for instance Pd$_2$(dba)$_3$.

Scheme C.2

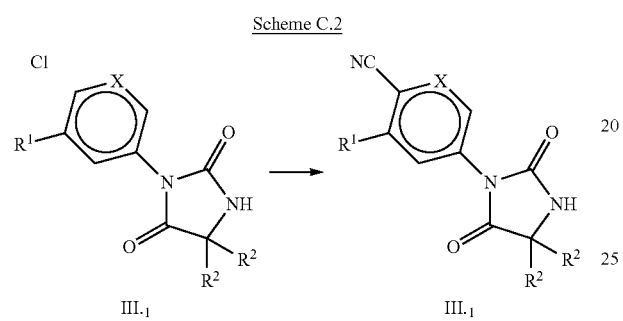

C.2.a) Preparation of Compounds of General Formula III.$_{1.1}$:

Compounds of general formula III.$_{1.1}$ can be prepared as shown in the scheme C.2.a., below. Compounds of general formula III.$_{1.1}$ in which R$^1$ is CF3, X is N and R$^2$ is as defined above can be prepared by reaction of a compound of general formula IV.$_2$ in which R$^1$ is CF$_3$, X is NH and Gf$_1$ is an atom of iodine or bromine and an hydantoin of general formula V.$_1$ in which R$^2$ is as defined above. The reaction can be conducted at a temperature between 80 and 150° C. in a polar aprotic solvent, for instance dimethylformamide. The reaction can be conducted in presence of copper derivative, for instance copper oxide.

Scheme C.2.a

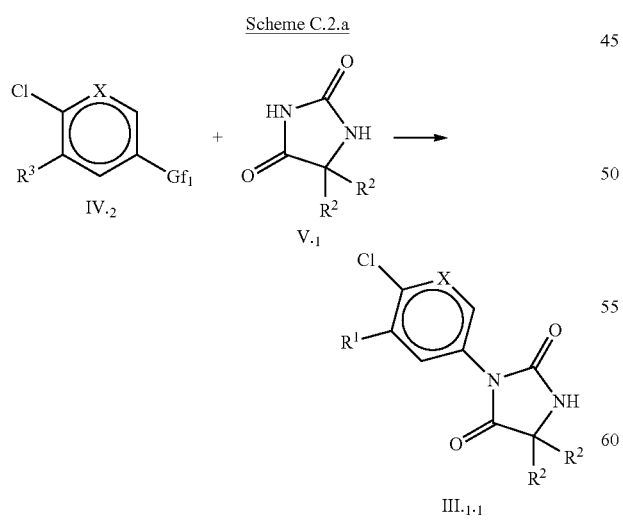

C.3) Preparation of Compounds of General Formula III.$_2$:

Compounds of general formula III.$_2$ can be prepared as shown in the scheme C.3, below. Compounds of general formula III.$_2$ in which R$^3$, R$^4$ and R$^5$ are as defined above can be prepared by reaction of an hydantoin of general formula V.$_2$ in which R$^3$ is as defined above and a compound of general formula IV.$_3$ in which R$^4$ and R$^5$ are as defined above and Gf$_2$ is an atom of iodine or bromine. The reaction can be conducted at a temperature between 80 and 150° C. in a polar aprotic solvent such as for instance dimethylformamide. The reaction can be conducted in presence of copperderivative such as for instance copper oxide.

Scheme C.3

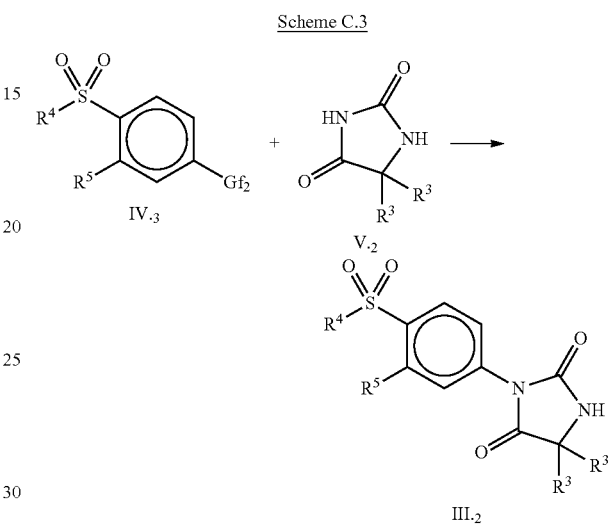

D) Preparation of Compounds of General Formula IV.$_1$, IV.$_2$ and IV.$_3$:

D.1) Preparation of Compounds of General Formula IV.$_1$:

Compounds of the general formula IV.$_1$ in which X is CH are commercially available, such as for instance 4-iodo-2-(trifluoromethyl)benzonitrile.

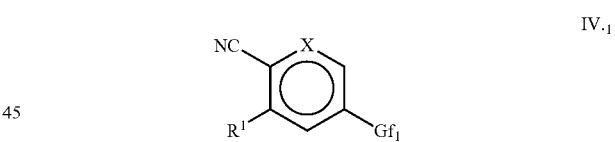

D.2) Preparation of Compounds of General Formula IV.$_2$:

Compounds of general formula IV.$_2$ can be prepared as shown in the scheme D.2, below. Compounds of general formula IV.$_2$ in which R$^1$ is CF$_3$, X is N and Gf$_1$ is an iodine atom can be prepared by treatment of a compound of general formula IV.$_{2.1}$ in which R$^1$ is CF$_3$, X is N and Gf$_1$ is an iodine atom with a chlorinating agent as for instance POCl$_3$. The reaction can be conducted at a temperature between 100 and 150° C.

Scheme D.2

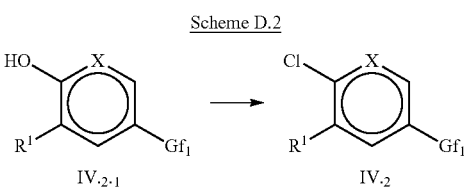

D.2.1) Preparation of Compounds of General Formula IV.$_{2.1}$:

Compounds of general formula IV.$_{2.1}$ can be prepared as described in the scheme D.2.1, below. Compounds of general formula IV.$_{2.1}$ in which R$^1$ is CF3, X is N and Gf$_1$ is an iodine atom can be prepared by treatment of a compound of general formula IV.$_{2.1.1}$ in which R$^1$ is CF3 and X is N by an iodinating agent such as for instance N-iodosuccinimide. The reaction can be conducted is a polar aprotic solvent, for instance dimethylformamide or acetonitrile. The reaction can be conducted at a temperature between 50 and 100° C.

Scheme D.2.1

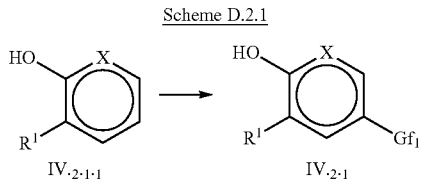

D.3) Preparation of Compounds of General Formula IV.$_3$:

Compounds described in the general formula IV.$_3$ can be prepared as shown in the scheme D.3, below. Compounds of the general formula IV.$_3$ in which R$^4$ and R$^5$ are as defined above and Gf$_2$ is an iodine atom can be prepared by treatment of a compound of general formula IV.$_{3.1}$ in which R$^4$ and R$^5$ are as defined above and Gf$_2$ is an iodine atom by an oxidizing agent such as for instance oxone. The reaction can be conducted at a temperature between 50 and 100° C. in a protic solvent such as for instance methanol or water.

Scheme D.3

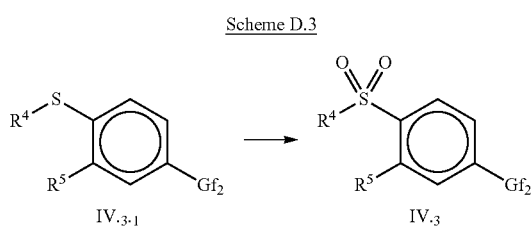

D.3.1) Preparation of Compounds of General Formula IV.$_{3.1}$:

Compounds of general formula IV.$_{3.1}$ can be prepared as described in the scheme D.3.1, below. Compounds of general formula IV.$_{3.1}$ in which R$^4$ and R$^5$ are as defined above and Gf$_2$ is an iodine atom can be prepared by treatment of a compound of general formula IV.$_{3.1.1}$ in which R$^5$ is as defined above, Gf$_2$ is an iodine atom and Gf$_3$ is a leaving group such as for instance a fluorine atom, by a compound of the general formula VI.$_1$ in which R$^4$ is as defined above. The reaction can be conducted in a polar protic solvent such as for instance dimethylformamide or acetonitrile. The reaction can be conducted at a temperature between 20 and 100° C.

Scheme D.3.1

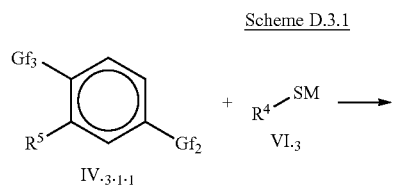

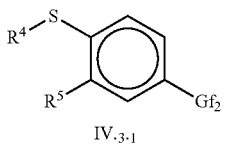

E) Preparation of Compounds of General Formula V.$_1$ or V.$_2$

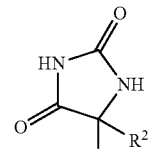

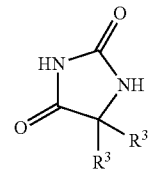

Non commercially available hydantoins of the general formula V.$_1$ or V.$_2$ in which R$^2$ and R$^3$ are as defined above can be prepared, for example, according to the methods described in. *J. Med. Chem.* 1984, 27 (12), 1663-8.

A subject of the present application is also the use of a compound of formula (I) according to the present invention, for the preparation of a medicament intended to treat proliferative diseases, preferentially cancers, very preferentially hormone-dependent cancers or cancers expressing androgen receptors, or prostate and breast cancers and very preferentially prostate cancers.

The pharmaceutical composition can be in the form of a solid, for example powders, granules, tablets, gelatin capsules. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, as well as their mixtures, in varying proportions, in water added to pharmaceutically acceptable oils or fats. The sterile liquid compositions can be used for intramuscular, intraperitoneal or sub-cutaneous injections and the sterile compositions can also be administered by intravenous route.

All the technical and scientific terms used in the present text have the meaning known to a person skilled in the art. Moreover, all the patents (or patent applications) as well as the other bibliographical references are incorporated by way of reference.

Experimental Part

Following the definitions of the variables R$^1$, R$^2$, R$^3$, R$^4$, R$^5$ and X, the compounds according to the invention can be prepared according to the different methods described above.

The NMR analyses of Examples 1 to 3 were carried out on a 400 MHz Bruker-Avance II spectrometer.

The examples are presented in order to illustrate the above procedures and should in no event be considered as a limit to the scope of the invention.

The terminology used for the nomenclature of the compounds below and the examples is the IUPAC terminology.

Example 1: (Z)-4-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2,5-dioxoimidazolidin-1-yl)-2-(trifluoromethyl)benzonitrile Step A. 4-(4,4-dimethyl-2,5-dioxoimidazolidin-1-yl)-2-(trifluoromethyl)benzonitrile To a mixture of 4-iodo-2-(trifluoromethyl)benzonitrile (51 g, 171.7 mmol) and $Cu_2O$ (24.5 g, 172 mmol) in DMF (500 mL) was added 5,5-dimethylimidazolidine-2,4-dione (33 g, 255 mmol). The mixture was heated at 150° C. for 12 hours and cooled to room temperature. The reaction mixture was filtered through a pad of Celite. The filtrate was concentrated under reduced pressure to about 50 mL. The residue was poured into ice-water (800 mL) and stirred at room temperature for 30 minutes. To the mixture was added 28% aqueous ammonia solution (60 mL) and the resulting blue suspension was stirred for 0.5 hours. The precipitated solid was collected by filtration and washed with THF (50 mL) to afford 4-(4,4-dimethyl-2,5-dioxoimidazolidin-1-yl)-2-(trifluoromethyl)benzonitrile as a pale white solid (50 g, 98%). LCMS (ESI) m/z: 298 $[M+H]^+$.

Step B. (Z)-4-(3-(4-chlorobut-2-en-1-yl)-4,4-dimethyl-2,5-dioxoimidazolidin-1-yl)-2-(trifluoromethyl)benzonitrile To a mixture of 4-(4,4-dimethyl-2,5-dioxoimidazolidin-1-yl)-2-(trifluoromethyl)benzonitrile (50 g, 168.4 mmol) and $Cs_2CO_3$ (110 g, 336.7 mmol) in acetonitrile (500 mL) at 25° C. was dropped a solution of (Z)-1,4-dichlorobut-2-ene (104 g, 842 mmol) in acetonitrile (200 mL) and heated at 75° C. for 2 hours. The reaction mixture was cooled to room temperature and filtered. The cake was washed with $CH_3CN$ (50 mL). The filtrate was concentrated under reduced pressure. The residue was purified by silica gel chromatography using EtOAc/petroleum ether (1:10) as eluting solvents to afford (Z)-4-(3-(4-chlorobut-2-en-1-yl)-4,4-dimethyl-2,5-dioxoimidazolidin-1-yl)-2-(trifluoromethyl)benzonitrile as a white solid (39 g, 60%). LCMS (ESI) m/z: 386 $[M+H]^+$.

Step C. (4-bromo-2-(trifluoromethyl)phenyl)(methyl)sulfane

A mixture of 4-bromo-1-fluoro-2-(trifluoromethyl)benzene (5.81 g, 23.9 mmol) and sodium methanethiolate (25% aqueous solution, 9.7 mL, 31.1 mmol) in DMF (20 mL) was stirred at 50° C. for 2 hours. The reaction mixture was cooled to room temperature, water (120 mL) was added and the resulting mixture was extracted with ethyl acetate (50 mL×3). The extracts were combined, washed with brine (50 mL×2), dried over magnesium sulfate, filtered, and concentrated under reduced pressure to afford (4-bromo-2-(trifluoromethyl)phenyl)(methyl)sulfane as a yellow oil (6.09 g, 94%), which was used in the next step without further purification.

Step D. 4-bromo-1-(methylsulfonyl)-2-(trifluoromethyl)benzene

A mixture of (4-bromo-2-(trifluoromethyl)phenyl)(methyl)sulfane (5 g, 18.4 mmol) and oxone (33.7 g, 55.2 mmol) in MeOH/water (50 mL/50 mL) was stirred at 40° C. overnight. The reaction mixture was concentrated under reduced pressure to remove MeOH. The resulting aqueous mixture was extracted with ethyl acetate (40 mL×3). The extracts were combined, washed with brine (50 mL), dried over magnesium sulfate, filtered and concentrated under reduced pressure. The residue was purified by silica gel chromatography petroleum ether:EtOAc (3:2) as eluting solvents to afford 4-bromo-1-(methylsulfonyl)-2-(trifluoromethyl)benzene as a white solid (4.35 g, 78%), which was used for the next step without further purification. LCMS (ESI) m/z: 303.0 $[M+H]^+$.

Step E. 5,5-dimethyl-3-(4-(methylsulfonyl)-3-(trifluoromethyl)phenyl)imidazolidine-2,4-dione A mixture of 4-bromo-1-(methylsulfonyl)-2-(trifluoromethyl)benzene (3.03 g, 10 mmol), 5,5-dimethyl imidazolidine-2,4-dione (1.41 g, 11 mmol), and $Cu_2O$ (1.76 g, 12.3 mmol) in DMF (8 mL) was heated at 145° C. overnight. The reaction mixture was cooled to room temperature and filtered. The filtrate was poured into water (50 mL) and extracted with ethyl acetate (25 mL×3). The extracts were combined, washed with brine (50 mL), dried over magnesium sulfate, filtered, and concentrated under reduced pressure to afford 5,5-dimethyl-3-(4-(methylsulfonyl)-3-(trifluoromethyl)phenyl)imidazolidine-2,4-dione as a pale white solid (2.92 g, 83%), which was used for the next step without further purification. LCMS (ESI) m/z: 351.1 [M+H]+.

Step F. (Z)-4-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2,5-dioxoimidazolidin-1-yl)-2-(trifluoromethyl)benzonitrile Under an atmosphere of nitrogen, a suspension of 5,5-dimethyl-3-(4-(methylsulfonyl)-3-(trifluoromethyl)phenyl)imidazolidine-2,4-dione (7.3 g, 20.8 mmol), (Z)-4-(3-(4-chlorobut-2-en-1-yl)-4,4-dimethyl-2,5-dioxoimidazolidin-1-yl)-2-(trifluoromethyl)benzonitril e (8 g, 20.8 mmol), $K_2CO_3$ (2.9 g, 20.8 g) and acetonitrile (80 mL) was stirred at reflux during 10 hours. After cooling, the reaction mixture was filtered, the precipitate was washed with acetonitrile (10 mL) and the combined filtrates were concentrated under vacuum. To the residue, water (150 mL) and ethyl acetate (150 mL) were added. After decantation, the organic layer was removed and the aqueous layer was extracted with ethyl acetate (2×150 mL). The combined organic layers were dried over magnesium sulfate and concentrated under reduce pressure. The residue was purified by column chromatography on silica gel and eluted with dichloromethane/ethyl acetate-95/5 to afford (Z)-4-(3-(4-(5,5-dimethyl-3-(4-(methyl sulfonyl)-3-(trifluoromethyl)phenyl)-2,4-dioxoimidazolidin-1-yl)but-2-en-1-yl)-4,4-dimethyl-2,5-dioxoimidazolidin-1-yl)-2-(trifluoromethyl)benzonitrile as pale white solid (10.6 g, 73%).

1H NMR (500 MHz, CDCl3) δ (ppm) 8.40 (d, J=8.0 Hz, 1H), 8.22 (d, J=1.5 Hz, 1H), 8.15 (d, J=1.5 Hz, 1H), 8.05 (dd, J=9.0 and 1.5 Hz, 1H), 8.00 (dd, J=8.5 and 1.5 Hz, 1H), 7.93 (d, J=8.5 Hz, 1H), 5.63-5.69 (m, 2H), 4.24 (t, J=4.0 Hz, 4H), 3.20 (s, 3H), 1.59 (s, 6H), 1.58 (s, 6H); LCMS (ESI) m/z: 700.0 [M+H]+.

Example 2: (Z)-5-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2,5-dioxoimidazolidin-1-yl)-3-(trifluoromethyl)picolinonitrile Step A. 5-iodo-3-(trifluoromethyl)pyridin-2-ol A mixture of 3-(trifluoromethyl)pyridin-2-ol (3.0 g, 18.5 mmol) and N-iodosuccinimide (4.2 g, 18.5 mmol) in acetonitrile (25 mL) and DMF (25 mL) was heated at 80° C. for 2 hours. After the reaction mixture was cooled to room temperature, water was added and the resulting mixture was extracted with ethyl acetate (70 mL×2). The extracts were combined, washed with brine (120 mL×3), dried over sodium sulfate, filtered, and concentrated under reduced pressure to afford 5-iodo-3-(trifluoromethyl)pyridin-2-ol as a yellow solid (4.0 g, 74%). $^1$H NMR (500 MHz, CDCl$_3$) δ (ppm) 13.37 (bs, 1H), 7.98 (d, J=2.0 Hz, 1H), 7.85 (d, J=2.0 Hz, 1H); LCMS (ESI) m/z: 290 [M+H]$^+$.

Step B. 2-chloro-5-iodo-3-(trifluoromethyl)pyridine

A suspension of 5-iodo-3-(trifluoromethyl)pyridin-2-ol (3.0 g, 10.4 mmol) in POCl$_3$ (8 mL) was heated at 100° C. overnight. After cooling down to room temperature, the mixture was poured into ice (50 g). The resulting aqueous layer was neutralized by Na$_2$CO$_3$ and extracted with ethyl acetate (70 mL×2). The extracts were combined, dried over sodium sulfate, filtered, and concentrated under reduced pressure. The residue was purified by silica gel chromatography using petroleum ether:EtOAc (100:1-4:1) as eluting solvents to afford 2-chloro-5-iodo-3-(trifluoromethyl)pyridine as a white solid (2.0 g, 63%). $^1$H NMR (500 MHz, CDCl$_3$) δ (ppm) 8.78 (d, J=2.0 Hz, 1H), 8.28 (d, J=2.0 Hz, 1H).

Step C. 3-(6-chloro-5-(trifluoromethyl)pyridin-3-yl)-5,5-dimethylimidazolidine-2,4-dione To a mixture of 2-chloro-5-iodo-3-(trifluoromethyl)pyridine (1.4 g, 4.5 mmol) in DMF (10 mL) was added 5,5-dimethylimidazolidine-2,4-dione (637 mg, 5.0 mmol) and Cu$_2$O (1.6 g, 11.4 mmol) and heated at 150° C. overnight. The reaction mixture was cooled to room temperature and filtered. The filtrate was poured into water (70 mL), 28% aqueous ammonia solution (6 mL) was added, and the resulting mixture was extracted with ethyl acetate (70 mL×2). The extracts were combined, washed with brine (100 mL×3), dried over sodium sulfate, filtered, and concentrated under reduced pressure. The residue was purified by silica gel chromatography using petroleum ether:EtOAc (10:1~1:1) as eluting solvents to afford 3-(6-chloro-5-(trifluoromethyl)pyridin-3-yl)-5,5-dimethylimidazolidine-2,4-dione as a white solid (955 mg, 68%). LCMS (ESI) m/z: 308 [M+H]$^+$.

Step D. 5-(4,4-dimethyl-2,5-dioxoimidazolidin-1-yl)-3-(trifluoromethyl)picolinonitrile To a solution of 3-(6-chloro-5-(trifluoromethyl)pyridin-3-yl)-5,5-dimethylimidazolidine-2,4-dione (950 mg, 3.1 mmol) in DMF (15 mL) was added Zn(CN)$_2$ (434 mg, 3.7 mmol), Pd$_2$(dba)$_3$ (283 mg, 0.31 mmol), and dppf (343 mg, 0.62 mmol). The mixture under N$_2$ atmosphere was heated at 140° C. overnight. After the reaction mixture was cooled to room temperature, it was filtered and the filtrate was extracted with ethyl acetate (70 mL×2). The extracts were combined, washed with brine (100 mL×3), dried over sodium sulfate, filtered, and concentrated under reduced pressure. The residue was purified by silica gel chromatography using petroleum ether:EtOAc (4:1~1:1) as eluting solvents to afford 5-(4,4-dimethyl-2,5-dioxoimidazolidin-1-yl)-3-(trifluoromethyl)picolinonitrile as a brown solid (910 mg, 99%). LCMS (ESI) m/z: 299 [M+H]$^+$.

Step E. (Z)-5-(3-(4-chlorobut-2-en-1-yl)-4,4-dimethyl-2,5-dioxoimidazolidin-1-yl)-3-(trifluoromethyl)picolinonitrile To a mixture of 5-(4,4-dimethyl-2,5-dioxoimidazolidin-1-yl)-3-(trifluoromethyl)picolino-nitrile (1.1 g, 3.65 mmol) and Cs$_2$CO$_3$ (2.4 g, 7.3 mmol) in acetonitrile (20 mL) at 25° C. was dropped a solution of (Z)-1,4-dichlorobut-2-ene (2.28 g, 18.3 mmol) in acetonitrile (2 mL) and heated at 75° C. for 2 hours. The reaction mixture was cooled down to room temperature, filtered, and washed with acetonitrile. The filtrate was concentrated under reduced pressure. The residue was purified by silica gel chromatography using petroleum ether:EtOAc (10:1~4:1) as eluting solvents to afford (Z)-5-(3-(4-Chlorobut-2-en-1-yl)-4,4-dimethyl-2,5-dioxoimidazolidin-1-yl)-3-(trifluoromethyl)picolinonitrile as a light yellow solid (780 mg, 56%). LCMS (ESI) m/z: 387 [M+H]$^+$.

Step F. (Z)-5-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2,5-dioxoimidazolidin-1-yl)-3-(trifluoromethyl)picolinonitrile A mixture of (Z)-5-(3-(4-chlorobut-2-enyl)-4,4-dimethyl-2,5-dioxoimidazolidin-1-yl)-3-(trifluoromethyl)picolinonitrile (190 mg, 0.51 mmol), K$_2$CO$_3$ (177 mg, 1.28 mol), and 5,5-dimethyl-3-(4-(methyl sulfonyl)-3-(trifluoromethyl)phenyl)imidazolidine-2,4-dione (150 mg, 0.43 mmol) in DMF (5 mL) was stirred at 60° C. for 2 hours. The reaction mixture was filtered and the filtrate was concentrated under reduced pressure. The residue was purified by preparative HPLC to afford (Z)-5-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2,5-dioxoimidazolidin-1-yl)-3-(trifluoromethyl)picolinonitrile as a white solid (160 mg, 20%).

1HNMR (500 MHz, DMSO-d6) δ (ppm) 9.21 (d, J=2.0 Hz, 1H), 8.64 (d, J=2.0 Hz, 1H), 8.37 (d, J=9.0 Hz, 1H), 8.22 (d, J=1.5 Hz, 1H), 8.10 (d, J=9.0 Hz, 1H), 5.61-5.62 (m, 2H), 4.21-4.23 (m, 4H), 3.34 (s, 3H), 1.52 (s, 6H), 1.51 (s, 6H); LCMS (ESI) m/z: 701.2 [M+H]$^+$.

Example 3: (Z)-4-(4,4-dimethyl-3-(4-(3-(4-(methylsulfonyl)-3-(trifluoromethyl)phenyl)-2,4-dioxoimidazolidin-1-yl)but-2-en-1-yl)-2,5-dioxoimidazolidin-1-yl)-2-(trifluoromethyl)benzonitrile Step A. 3-(4-(methylsulfonyl)-3-(trifluoromethyl)phenyl)imidazolidine-2,4-dione A mixture of 4-bromo-1-(methylsulfonyl)-2-(trifluoromethyl)benzene (1 g, 3.31 mmol), imidazolidine-2,4-dione (0.50 g, 4.97 mmol), and Cu$_2$O (0.48 g, 3.36 mmol) in DMF (10 mL) was heated at 150° C. for 4 hours. The reaction mixture was poured into ice-water (200 mL) and stirred at room temperature for 30 minutes. To the mixture was added a 28% aqueous ammonia solution (5 mL) and stirred for 1 hour. The reaction mixture was filtered. The crude product was washed with water and THF to afford 3-(4-(methylsulfonyl)-3-(trifluoromethyl)phenyl)imidazolidine-2,4-dione as a white solid (350 mg, 33%). LCMS (ESI) m/z: 323.1 [M+H]$^+$.

Step B. (Z)-4-(4,4-dimethyl-3-(4-(3-(4-(methylsulfonyl)-3-(trifluoromethyl)phenyl)-2,4-dioxoimidazolidin-1-yl)but-2-en-1-yl)-2,5-dioxoimidazolidin-1-yl)-2-(trifluoromethyl)benzonitrile A mixture of (Z)-4-(3-(4-chlorobut-2-en-1-yl)-4,4-dimethyl-2,5-dioxoimidazolidin-1-yl)-2-(trifluoromethyl) benzonitrile (420 mg, 1.09 mmol), 3-(4-(methylsulfonyl)-3-(trifluoromethyl)phenyl)imidazolidine-2,4-dione (350 mg, 1.09 mmol), and $K_2CO_3$ (560 mg, 4.06 mmol) in acetonitrile (5 mL) was heated at 60° C. for 1 hour. The reaction mixture was quenched with water and extracted with ethyl acetate. The extracts were combined, washed with brine, dried over sodium sulfate, filtered, and concentrated under reduced pressure. The residue was purified by preparative HPLC to afford (Z)-4-(4,4-dimethyl-3-(4-(3-(4-(methyl sulfonyl)-3-(trifluoromethyl)phenyl)-2,4-dioxoimidazolidin-1-yl)but-2-en-1-yl)-2,5-dioxoimidazolidin-1-yl)-2-(trifluoromethyl) benzonitrile as a white solid (62 mg, 9%).
$^1$H NMR (500 MHz, DMSO-$d_6$) δ (ppm) 8.38-8.32 (m, 2H), 8.20 (s, 1H), 8.14 (s, 1H), 8.06 (d, J=10.0 Hz, 2H), 6.72-5.66 (m, 2H), 4.22-4.16 (m, 6H), 3.35 (s, 3H), 1.50 (s, 6H). LCMS (ESI) m/z: 672.1 [M+H]$^+$.

Pharmacological Study of the Compounds According to the Invention

Measurements of Anti-Proliferative Activities:

1. Anti-Proliferative Activity on LNCaP in Complete Medium

The anti-proliferative activity of the compounds of the present invention is determined on LNCaP in complete medium by applying the following experimental procedure:

The LNCaP cell type (ATCC, 1740) originates from a prostate carcinoma. This line expresses the androgen receptor and is hormone-dependent.

Maintenance of the LNCaP line is carried out in complete culture medium: RPMI, 10% of fetal calf serum, 2 mM glutamine, 100 U/ml penicillin, 0.1 mg/ml of streptomycin and 0.01M HEPES, 1 mM sodium pyruvate, 40% of D-glucose.

Seeding the plates: The LNCaP line is seeded at 20,000 cells/well in 90 μl of complete medium in 96-well plates coated with poly-D-lysine (Biocoat, Costar).

Treatment of the cells: 24 h after the seeding, the cells are treated with 10 μl/well of compound diluted in the culture medium. The concentrations used are the following: 1 nM/10/30/100/300/1000/3000/10,000 nM. The cells are incubated for 144 h at 37° C., 5% $CO_2$.

Reading: After incubation for 6 days, cell proliferation was determined by Cell-Titer-Glow (CTG) Luminescent Cell Viability Assay.

Results: The experiments are carried out in duplicate and the best compounds are tested twice. A concentration value inhibiting the cell proliferation by 50% ($IC_{50}$) is calculated.

| Example No | LNCaP IC50 (nM) |
| --- | --- |
| 1 | 313 |
| 2 | 1592 |
| 3 | 1117 |
| Ex 21 of WO2010/119194 | 207 |

2. Anti-Proliferative Activity on DU145 in Complete Medium

DU145 is a prostate cancer cell line that does not express androgen receptor. It is used to evaluate the selectivity of the compounds for androgen receptor expressing cells. No activity of the compounds is expected.

The cells of the DU145 line (ATCC HTB-81) are seeded at 800 cells/well in 90 μl of complete medium in 96-well plates coated with poly-D-lysine (Biocoat, Costar).

Treatment of the cells: 24 h after the seeding, the cells are treated with 10 μl/well of compound diluted in the culture medium. The concentrations used are the following: 1 nM/10/30/100/300/1000/3000/10,000 nM. The cells are incubated for 144 h at 37° C., 5% $CO_2$.

Reading: After incubation for 6 days, cell proliferation was determined by Cell-Titer-Glow (CTG) Luminescent Cell Viability Assay Results: The experiments are carried out in duplicate and the best compounds are tested twice. A concentration value inhibiting the cell proliferation by 50% ($IC_{50}$) is calculated.

| Example No | DU145 IC50 (nM) |
| --- | --- |
| 1 | >10000 |
| 2 | >10000 |
| 3 | >10000 |
| Ex 21 of WO2010/119194 | >10000 |

3. Anti-Proliferative Activity on VCaP in Complete Medium

The cells of the VCaP line (ATCC CRL-2876) are seeded at 20000 cells/well in 90 μl of complete medium in 96-well plates coated with poly-D-lysine (Biocoat, Costar).

Treatment of the cells: 24 h after the seeding, the cells are treated with 10 μl/well of compound diluted in the culture medium. The concentrations used are the following: 1 nM/10/30/100/300/1000/3000/10,000 nM. The cells are incubated for 144 h at 37° C., 5% $CO_2$.

Reading: After incubation for 9 days, cell proliferation was determined by Cell-Titer-Glow (CTG) Luminescent Cell Viability Assay Results: The experiments are carried out in duplicate and the best compounds are tested twice. A concentration value inhibiting the cell proliferation by 50% ($IC_{50}$) is calculated.

| Example No | VCaP IC50 (nM) |
| --- | --- |
| 1 | 551 |
| 2 | 1050 |
| Ex 21 of WO2010/119194 | 543 |

Measurement of Protein Expression of the Androgen Receptor

The cells of the LNCaP line are seeded at a rate of 2.5 million of cells per 10 cm Petri dish and maintained in 8 ml RPMI-1640 for 4 days. After 4 days incubation, 4 ml of medium were removed from the Petri dish and 5 ml fresh medium was added carefully. 1 ml of compounds 10-fold diluted in complete medium at concentrations from 3×10-6 M to 10-8 M. Cells were treated with the compounds for additional 3 days. The whole cell protein was extracted by Nuclear Extract kit and quantitated by the Bradford Protein Assay. The effect of compounds on AR levels in LNCaP cells was then determined by an AR ELISA kit. IC50 of Examples are listed below:

| Example No | IC50 AR destruction in LNCaP (nM) |
|---|---|
| 1 | 123 |
| 2 | 946 |
| Ex 21 of WO2010/119194 | 147 |

Evaluation of Solubility:

Test compounds were prepared as stock solutions at 100 mM in DMSO. The stock solutions were diluted, in duplicate, into 100 mM potassium phosphate buffer (pH 7.4) to a target concentration of 10 μM with a final DMSO concentration of 0.1%. The solutions were shaken at 1000 rpm for 1 hour at room temperature followed by centrifugation for 10 minutes at 1200 rpm to precipitate un-dissolved particles. The supernatants were transferred to new tubes and the samples were further prepared as follows:

Undiluted: 5 μL of supernatant to 95 μL of ACN containing internal standard (IS)

1:10 diluted: 10 μL of the supernatant into 90 μL K-buffer, mix, then transfer 5 μL of 1:10 diluted samples to 95 μL ACN containing IS 1:100 diluted: 10 μL of the supernatant into 990 μL K-buffer, mix, then transfer 5 μL of 1:100 diluted samples to 95 μL of ACN containing IS Samples (undiluted, 1:10 diluted, and 1:100 diluted) along with the standards were analyzed by LC-MS/MS.

Solubilities of Examples are listed below:

| Example No | Solubility (μM) |
|---|---|
| 1 | 2.66 |
| 2 | 0.14 |
| 3 | 0.53 |
| Ex 21 of WO2010/119194 | <0.02 |

The invention claimed is:

1. A compound of formula (I):

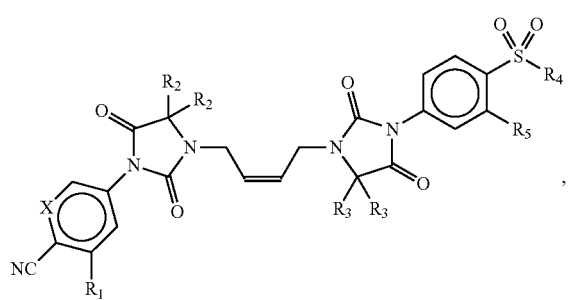

(I)

or a pharmaceutically acceptable salt thereof wherein:
$R^1$ is a —$CF_3$ group or a halogen atom;
each $R^2$ is individually a ($C_1$-$C_6$)alkyl group or the two $R^2$ groups together form a ($C_3$-$C_6$)cycloalkyl group;
X is CH or N;
each $R^3$ is individually a hydrogen atom or a ($C_1$-$C_6$) alkyl group or the two $R^3$ groups together form a ($C_3$-$C_6$)cycloalkyl group;
$R^4$ is a ($C_1$-$C_6$)alkyl group; and
$R^5$ is a —$CF_3$ group or an atom selected from the halogen group.

2. The compound of claim 1, wherein $R^2$ is a ($C_1$-$C_6$)alkyl group.

3. The compound of claim 2, wherein $R^2$ is a methyl group.

4. The compound of claim 1, wherein $R^3$ is a ($C_1$-$C_6$)alkyl group.

5. The compound of claim 4, wherein $R^3$ is a methyl group.

6. The compound of claim 1, wherein $R^4$ is a ($C_1$-$C_3$)alkyl group.

7. The compound of claim 6, wherein $R^4$ is a methyl group.

8. The compound of claim 6, wherein $R^4$ is an ethyl group.

9. The compound of claim 1, wherein $R^5$ is a —$CF_3$ group.

10. The compound of claim 1, wherein $R^1$ is a —$CF_3$ group.

11. The compound of claim 1, which is:
(Z)-4-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2,5-dioxoimidazolidin-1-yl)-2-(trifluoromethyl)benzonitrile, or a pharmaceutically-acceptable salt thereof;
(Z)-5-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2,5-dioxoimidazolidin-1-yl)-3-(trifluoromethyl)picolinonitrile, or a pharmaceutically-acceptable salt thereof; or
(Z)-4-(4,4-dimethyl-3-(4-(3-(4-(methylsulfonyl)-3-(trifluoromethyl)phenyl)-2,4-dioxoimidazolidin-1-yl) but-2-en-1-yl)-2,5-dioxoimidazolidin-1-yl)-2-(trifluoromethyl)benzonitrile, or a pharmaceutically-acceptable salt thereof.

12. The compound of claim 11 which is (Z)-4-(3-(4-(5,5-dimethyl-3-(4-(methylsulfonyl)-3-(trifluoromethyl)phenyl)-2,4-dioxoimidazolidin-1-yl)but-2-en-1-yl)-4,4-dimethyl-2,5-dioxoimidazolidin-1-yl)-2-(trifluoromethyl) benzonitrile, or a pharmaceutically acceptable salt thereof.

13. A pharmaceutical composition comprising a compound of claim 1 and a pharmaceutically acceptable support.

14. A method for treating prostate cancer comprising administering, to a subject in need thereof, a compound of claim 1.

* * * * *